(12) United States Patent
Roseway et al.

(10) Patent No.: US 9,046,884 B2
(45) Date of Patent: Jun. 2, 2015

(54) MOOD-ACTUATED DEVICE

(71) Applicant: Microsoft Corporation, Redmond, WA (US)

(72) Inventors: Asta J. Roseway, Bellevue, WA (US); Felecia A. Davis, Cambridge, MA (US); Erin A. Carroll, Mooresville, NC (US); Mary Czerwinski, Kirkland, WA (US); Diana L. Maclean, Palo Alto, CA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 179 days.

(21) Appl. No.: 13/732,323

(22) Filed: Dec. 31, 2012

(65) Prior Publication Data

US 2014/0188276 A1 Jul. 3, 2014

(51) Int. Cl.

| | |
|---|---|
| *G05B 15/00* | (2006.01) |
| *G05B 19/04* | (2006.01) |
| *A61B 5/00* | (2006.01) |
| *A61B 5/16* | (2006.01) |
| *G06F 19/00* | (2011.01) |
| *G06F 3/01* | (2006.01) |
| *A61B 5/024* | (2006.01) |
| *A61B 5/0402* | (2006.01) |

(Continued)

(52) U.S. Cl.
CPC . *G05B 19/04* (2013.01); *A61B 5/74* (2013.01); *A61B 5/024* (2013.01); *A61B 5/0402* (2013.01); *A61B 5/0533* (2013.01); *A61B 5/165* (2013.01); *A61B 5/486* (2013.01); *A61B 5/6802* (2013.01); *A61B 2560/0487* (2013.01); *A61M 2021/0044* (2013.01); *A61M 21/00* (2013.01); *A61M 2021/0022* (2013.01); *A61M 2021/0066* (2013.01); *A61M 2205/505* (2013.01); *G06F 19/3406* (2013.01); *G06F 3/011* (2013.01); *G06F 3/015* (2013.01); *G06F 3/016* (2013.01); *Y10S 901/01* (2013.01); *Y10S 901/02* (2013.01); *Y10S 901/20* (2013.01)

(58) Field of Classification Search
CPC ................................................ G06F 2203/011
See application file for complete search history.

(56) References Cited

U.S. PATENT DOCUMENTS 5,832,189 A * 11/1998 Tow .............................. 700/259
6,629,242 B2 * 9/2003 Kamiya et al. ................ 713/100

(Continued)

FOREIGN PATENT DOCUMENTS

EP           2196138 A2      6/2010

OTHER PUBLICATIONS

Tokuhisa, Satoru, "Aequorin: Design of a system for reduction of the user's stress in one day", Retrieved at <<http://ieeexplore.ieee.org/stamp/stamp.jsp?tp=&arnumber=5345410>>, In International Conference on Ultra-Modern Telecommunications & Workshops, Oct. 12, 2009, pp. 6.

(Continued)

*Primary Examiner* — Jonathan L Sample
(74) *Attorney, Agent, or Firm* — Sandy Swain; Judy Yee; Micky Minhas

(57) ABSTRACT

This document describes techniques and apparatuses for implementing a mood-actuated device. In various embodiments, indicators of an emotional state of a user are sensed, and a mood-actuated device is controlled to react based on the emotional state of the user. In some embodiments, the mood-actuated device includes a mechanical component that is configured to react by moving based on the emotional state of the user.

19 Claims, 9 Drawing Sheets

(51) Int. Cl.
*A61B 5/053* (2006.01)
*A61M 21/00* (2006.01)

(56) References Cited

U.S. PATENT DOCUMENTS

| | | | |
|---|---|---|---|
| 6,907,688 B2* | 6/2005 | Brint | 43/2 |
| 7,785,249 B2 | 8/2010 | Schachter et al. | |
| 8,004,391 B2 | 8/2011 | Cruz-Hernandez | |
| 8,509,972 B2* | 8/2013 | Shu | 701/21 |
| 2002/0120362 A1* | 8/2002 | Lathan et al. | 700/245 |
| 2003/0019671 A1* | 1/2003 | Inoue et al. | 180/8.1 |
| 2003/0088336 A1* | 5/2003 | Osawa | 700/245 |
| 2003/0109959 A1* | 6/2003 | Tajima et al. | 700/245 |
| 2006/0038745 A1 | 2/2006 | Naksen et al. | |
| 2006/0041332 A1* | 2/2006 | Sabe et al. | 700/245 |
| 2007/0021206 A1* | 1/2007 | Sunnen | 463/36 |
| 2007/0150099 A1* | 6/2007 | Lee et al. | 700/245 |
| 2007/0222344 A1* | 9/2007 | Kornbluh et al. | 310/800 |
| 2008/0077277 A1* | 3/2008 | Park et al. | 700/245 |
| 2008/0119959 A1* | 5/2008 | Park et al. | 700/245 |
| 2008/0195980 A1* | 8/2008 | Morris | 715/864 |
| 2008/0208016 A1 | 8/2008 | Hughes et al. | |
| 2008/0214944 A1 | 9/2008 | Morris et al. | |
| 2008/0269629 A1 | 10/2008 | Reiner | |
| 2008/0269958 A1 | 10/2008 | Filev et al. | |
| 2009/0002178 A1* | 1/2009 | Guday et al. | 340/573.1 |
| 2009/0040231 A1* | 2/2009 | Sano et al. | 345/474 |
| 2009/0265051 A1* | 10/2009 | Shu | 701/21 |
| 2010/0197184 A1 | 8/2010 | Browne et al. | |
| 2010/0324427 A1 | 12/2010 | Devot et al. | |
| 2011/0004577 A1* | 1/2011 | Jung et al. | 706/12 |
| 2011/0018717 A1* | 1/2011 | Takahashi | 340/573.1 |
| 2011/0054691 A1* | 3/2011 | Lee et al. | 700/259 |
| 2011/0095975 A1 | 4/2011 | Hwang et al. | |
| 2011/0183305 A1* | 7/2011 | Orbach | 434/236 |
| 2012/0022688 A1* | 1/2012 | Wong et al. | 700/253 |
| 2012/0115390 A1* | 5/2012 | Fuchiwaki et al. | 446/35 |
| 2012/0239196 A1* | 9/2012 | Olivier et al. | 700/259 |
| 2013/0022232 A1* | 1/2013 | Jacob et al. | 382/103 |
| 2013/0154980 A1* | 6/2013 | Byrnes et al. | 345/173 |
| 2014/0085181 A1 | 3/2014 | Roseway | |
| 2014/0099613 A1* | 4/2014 | Krauss et al. | 434/236 |

OTHER PUBLICATIONS

Cerutti, et al., "Analysis of sleep and stress profiles from biomedical signal processing in wearable devices", Retrieved at <<http://embc2006.njit.edu/pdf/2010_Cerutti.pdf>>, 28th IEEE Annual International Conference on Engineering in Medicine and Biology Society, Aug. 30, 2006, pp. 3.
Broek, et al., "Biofeedback Systems for Stress Reduction", Retrieved at <<http://doc.utwente.nl/79721/1/VandenBroek12Biofeedback_systems.pdf>>, International Conference on Health Informatics, Feb. 1, 2012, pp. 6.
Ferreira, Pedro, "Studying experiences of a real-time biofeedback system", Retrieved at <<http://www.mobilelifecentre.org/sites/default/files/pedromscthesis.pdf>>, Oct. 8, 2008, pp. 74.
"Affeciva", Retrieved at <<http://www.affectiva.com/>>, Retreived Date Nov. 2, 2012.
Arroyo, et al., "Emotion Sensors go to School", Retrieved at <<http://centerforknowledgecommunication.com/publications/recentPubsandAwards/2009/AIED%20SENSORS%20CameraReady.pdf>>, In Proceedings of the Conference on Artificial Intelligence in Education: Building Learning Systems that Care: From Knowledge Representation to Affective Modelling, Jul. 6, 2009, pp. 8.
Cai, et al., "Study on Driver Emotion in Driver-Vehicle-Environment Systems Using Multiple Networked Driving Simulators", Retrieved at <<http://www1.coe.neu.edu/~mourant/mourant/Publications_files/linlowa2007.pdf>>, In Driving Simulation Conference, Sep. 2007, pp. 8.
Cohen, et al., "Strategies for Measuring Stress in Studies of Psychiatric and Physical Disorders", Retrieved at <<http://www.psy.cmu.edu/~scohen/Cohen,%20S%20et%20al%20(1995).pdf>>, In Oxford University Press, Retrieved Date: Nov. 2, 2012, pp. 24
Healey, et al., "Detecting Stress during Real-World Driving Tasks Using Physiological Sensors", Retrieved at <<http://ieeexplore.ieee.org/stamp/stamp.jsp?tp=&arnumber=1438384>>, In IEEE Transactions on Intelligent Transportation Systems, vol. 6, Issue 2, Jun. 2005, pp. 11.
Hennessy, et al., "The Influence of Traffic Congestion, Daily Hassles, and Trait Stress Susceptibility on State Driver Stress: An Interactive Perspective", Retrieved at <<http://faculty.buffalostate.edu/hennesda/Hassles%20congestion%20&%20stress%20-%20JABR.pdf>>, In Journal of Applied Behavioral Research, vol. 5, Issue 2, Jul. 2000, pp. 18.
Isen, et al., "Positive Affect Facilitates Creative Problem Solving", Retrieved at <<http://www.ivk.tu-dresden.de/die_tu_dresden/fakultaeten/faukultaet_mathematik_und_naturwissenschaften/fachrichtung_psychologie/i1/allgpsy/lehre/lehreverstaltungen/bolte_lehre/ala/lsen_1987.pdf>>, In Journal of Personality and Social Psychology, vol. 52, Issue 6, Jun. 1987, pp. 10.
Krusche, et al., "Mindfulness Online: A Preliminary Evaluation of the Feasibility of a Web-Based Mindfulness Course and the Impact on Stress", Retrieved at <<http://bmjopen.bmj.com/content/2/3/e000803.full.pdf+html>>, In BMJ Open, vol. 2, Issue 3, May 21, 2012, pp. 7.
Kuliac, et al., "Anxiety Detection during Human-Robot Interaction", Retrieved at <<http://ieeexplore.ieee.org/stamp/stamp.jsp?tp=&arnumber=1545012>>, In Proceeding of IEEE/RSJ International Conference on Intelligent Robotics and Systems, Aug. 2, 2005, pp. 6.
McDuff, et al., "AffectAura: An Intelligent System for Emotional Memory", Retrieved at <<http://www.affectiva.com/assets/Q-Sensor-Microsoft-Publication.pdf>>, In Proceedings of the SIGCHI Conference on Human Factors in Computing Systems, May 5, 2012, pp. 10.
Morris, et al., "Crowdsourcing Collective Emotional Intelligence", Retrieved at <<http://arxiv.org/ftp/arxiv/papers/1204/1204.3481.pdf>>, In Collective Intelligence Conference, Apr. 16, 2012, pp. 8.
Nasoz, et al., "Affectively Intelligent and Adaptive Car Interfaces", Retrieved at <<http://www.eecs.ucf.edu/~gitars/cap6671/StudentPapers/affective.pdf>>, In International Journal of Information Sciences, vol. 180, Issue 20, Oct. 2010, pp. 20.
Paredes, et al., "CalmMeNow: Exploratory Research and Design of Stress Mitigating Mobile Interventions", Retrieved at <<http://hci.berkeley.edu/cs260-fall10/images/1/19/DraftPaper-ParedesChan.pdf>>, In Proceedings of Extended Abstracts on Human Factors in Computing Systems, May 7, 2011, pp. 6
Reiner, Robert, "Integrating a Portable Biofeedback Device into Clinical Practice for Patients with Anxiety Disorders: Results of a Pilot Study", Retrieved at <<http://stresseraser-uk.com/clinical-research/Reiner%20R%20Journal%20of%20Applied%20Psychophysiology%20%20Biofeedback.pdf>>, In Journal of Applied Psychophysiology and Biofeedback, vol. 33, Issue 1, Mar. 2008, pp. 7
Riener, at al., "Heart on the Road: HRV Analysis for Monitoring a Driver's Affective State", Retrieved at <<http://www.pervasive.jku.at/Research/Publications/_Documents/2009_Heart%20on%20the%20road%20-%20HRV%20analysis%20for%20monitoring%20a%20drivers%20affective%20state_Riener.pdf>>, In Proceedings of the 1st International Conference on Automotive User Interfaces and Interactive Vehicular Applications, Sep. 21, 2009, pp. 8
Rusting, et al., "Regulating Responses to Anger: Effects of Rumination and Distraction on Angry Mood", Retrieved at <<http://www.yale.edu/snhlab/Health%20Consequences_files/Rusting%20%26%20Nolen-Hoeksema,%201998.pdf>>, In Journal of Personality and Social Psychology, vol. 74, No. 3, Mar. 1998, pp. 14.
"StressEraser", Retrieved at <<http://stresseraser.com/>>, Retrieved Date Nov. 5, 2012, pp. 10.
"WildDivine", Retrieved at <<http://www.wilddivine.com/>>, Retrieved Date Nov. 5, 2012, pp. 12.
"International Search Report & Written Opinion for PCT Application No. PCT/US2013/059334", Mailed Date: Feb. 5, 2014, Filed Date: Sep. 12, 2013, 9 Pages.

(56) References Cited

OTHER PUBLICATIONS

"Flame Resistance of Wool", retrieved from <http://www.csiro.au/files/files/p9z9.pdf> on Aug. 24, 2012, 3 pages.
"GER: Mood Sweater", *Sensoree*, Retrieved from: <http://sensoree.com/artifacts/ger-mood-sweater/> on Sep. 28, 2012,(2011), 2 pages.
Baik, Kyuhee "Sensory Elegance: A Q&A with Conceptual Fashion Designer Ying Gao", retrieved from <http://thecreatorsproject.com/blog/sensory-elegance-a-qa-with-conceptual-fashion-designer-ying-gao> on Aug. 24, 2012, (May 16, 2012), 9 pages.
Berzowska, Joanna et al., "Kukkia and Vilkas: Kinetic Electronic Garments", *In Proceedings of Ninth IEEE International Symposium on Wearable Computers*, retrieved from <http://ieeexplore.ieee.org/stamp/stamp.jsp?tp=&arnumber=1550790>,(Oct. 18, 2005), 4 pages.
Brokenshire, Paul et al., "Heart on Sleeve: Visualizing Human Touch and Emotion through Wearable Technology", retrieved from <http://www.sfu.ca/~paulb/iat320/Touch_Powers_Heart.pdf>, (Aug. 24, 2012), 5 pages.
Corzilus, Maarten et al., "A Real-time Emotion Mirror", retrieved from <http://www.inf.unideb.hu/~sajolevente/papers2/emotion/emotion_mirror.pdf>, (Feb. 15, 2006), 9 pages.
De Magalhaes, Sergio T., et al., "Wearable Authentication Device with Biometrical Intrusion Prevention System", *IADIS Virtual Multi Conference on Computer Science and Information Systems*, retrieved from <http://www.iadis.net/dl/final_uploads/200504H001.pdf>,(Apr. 11, 2005), pp. 463-470.
Hallnas, Lars et al., "Slow Technology—Designing for Reflection", retrieved from <http://citeseerx.ist.psu.edu/viewdoc/download;jsessionid=C3642543CB6985AA98B687CAD502E16A?doi=10.1.1.21.5239&rep=rep1&type=pdf>, (Aug. 2001), 12 pages.
Katsis, Christos D., et al., "Toward Emotion Recognition in Car-Racing Drivers: A Biosignal Processing Approach", *IEEE Transactions on Systems, Man, and Cybernetics—Part a: Systems and Humans*, vol. 38, No. 3, retrieved from <http://medlab.cc.uoi.gr/Papers_Fotiadis/A93.pdf>, (May 3, 2008), pp. 502-512.
Mims, Christopher "Robot Swarms Aim to Bring Buildings to Life", retrieved from <http://www.bbc.com/future/story/20120717-bringing-buildings-to-life> on Aug. 24, 2012, (Jul. 18, 2012), 8 pages.

Mura, Gokhan "Wearable Technologies for Emotion Communication", *Middle East Technical University (METU) Journal of the Faculty of Architecture*, 25:1, retrieved from <http://jfa.arch.metu.edu.tr/archive/0258-5316/2008/cilt25/sayi_1/153-161.pdf> on Aug. 24, 2012,(Jan. 2008), pp. 153-161.
Negropante, Nicholas "Soft Architecture Machines", retrieved from <http://dl.dropbox.com/u/2163252/negroponte-softarchitecturemachines.pdf> on Aug. 24, 2012, (1975), 128 pages.
Picard, Rosalind W., et al., "The Galvactivator: A Glove that Senses and Communicates Skin Conductivity", In *9th International Conference on Human-Computer Interaction*, retrieved from <http://affect.media.mit.edu/pdfs/TR-542/TR-542.pdf>,(Aug. 2001), 6 pages.
Pioggia, Giovanni et al., "Facial Automaton for Conveying Emotions as a Social Rehabilitation Tool for People with Autism", *Rehabilitation Robotics, Vienna: I-Tech Education and Publishing*, retrieved from <http://cdn.intechweb.org/pdfs/571.pdf>,(Aug. 2007), pp. 431-452.
Russell, James A., "A Circumplex Model of Affect", In *Journal of Personality and Social Psychology*, vol. 29, Issue 6, retrieved from <https://www2.bc.edu/~russeljm/publications/Russell1980.pdf>,(Dec. 1980), pp. 1161-1178.
Scheirer, Jocelyn et al., "Affective Objects", In *Mit Media Laboratory Perceptual Computing Section Technical Report No. 524*, retrieved from <http://vismod.media.mit.edu/tech-reports/TR-524.pdf> on Aug. 24, 2012, 19 pages.
"International Search Report & Written Opinion for PCT Patent Application No. PCT/US2013/077900", Mailed Date: Mar. 17, 2014, Filed Date: Dec. 27, 2013, 15 Pages.
Black, Lucy, "Wearable Tech to Help Control Stress", Jul. 6, 2012, Available at: http://www. i-programmer.info/news/91-hardware/4318-wearable-tech-to-help-control-stress.html.
MacLean, et al., "MoodWings: A Wearable Biofeedback Device for Real-Time Stress Intervention", In International Conference on PErvasive Technologies Related to Assistive Environments, May 29, 2013, 8 Pages.
"Non-Final Office Action", U.S. Appl. No. 13/732,280, Jun. 20, 2014, 9 pages.
"Final Office Action", U.S. Appl. No. 13/732,280, Dec. 17, 2014, 13 pages.

\* cited by examiner

MOOD-ACTUATED DEVICE

BACKGROUND

Stress has a wide range of negative impacts on people, ranging from declines in real-time task performance to development of chronic health conditions. Despite the increasing availability of sensors and methods for detecting stress, there are very few existing stress intervention applications. Further, gaps still exist between what a person perceives as stress, and what is actually going on in the person's body.

SUMMARY

This document describes techniques and apparatuses for implementing a mood-actuated device. In various embodiments, indicators of an emotional state of a user are sensed, and a mood-actuated device is controlled to react based on the emotional state of the user. In some embodiments, the mood-actuated device includes a mechanical component that is configured to react by moving based on the emotional state of the user.

This summary is provided to introduce simplified concepts in a simplified form that are further described below in the Detailed Description. This summary is not intended to identify essential features of the claimed subject matter, nor is it intended for use in determining the scope of the claimed subject matter.

BRIEF DESCRIPTION OF THE DRAWINGS

Embodiments of techniques and apparatuses for a mood-actuated device are described with reference to the following drawings. The same numbers are used throughout the drawings to reference like features and components.

DETAILED DESCRIPTION

Overview

This document describes techniques and apparatuses for implementing a mood-actuated device. In various embodiments, a bio sensor senses indicators of an emotional state of a user, or a group of users. The bio sensor can be any type of sensor, such as a heart rate monitor, an electrocardiography monitor, or a galvanic skin response monitor. A microcontroller causes a mood-actuated device to react based on the emotional state of the user. In some embodiments, the mood-actuated device includes a mechanical component that is configured to react by moving based on the emotional state of the user.

Example Environment

Figure 1:
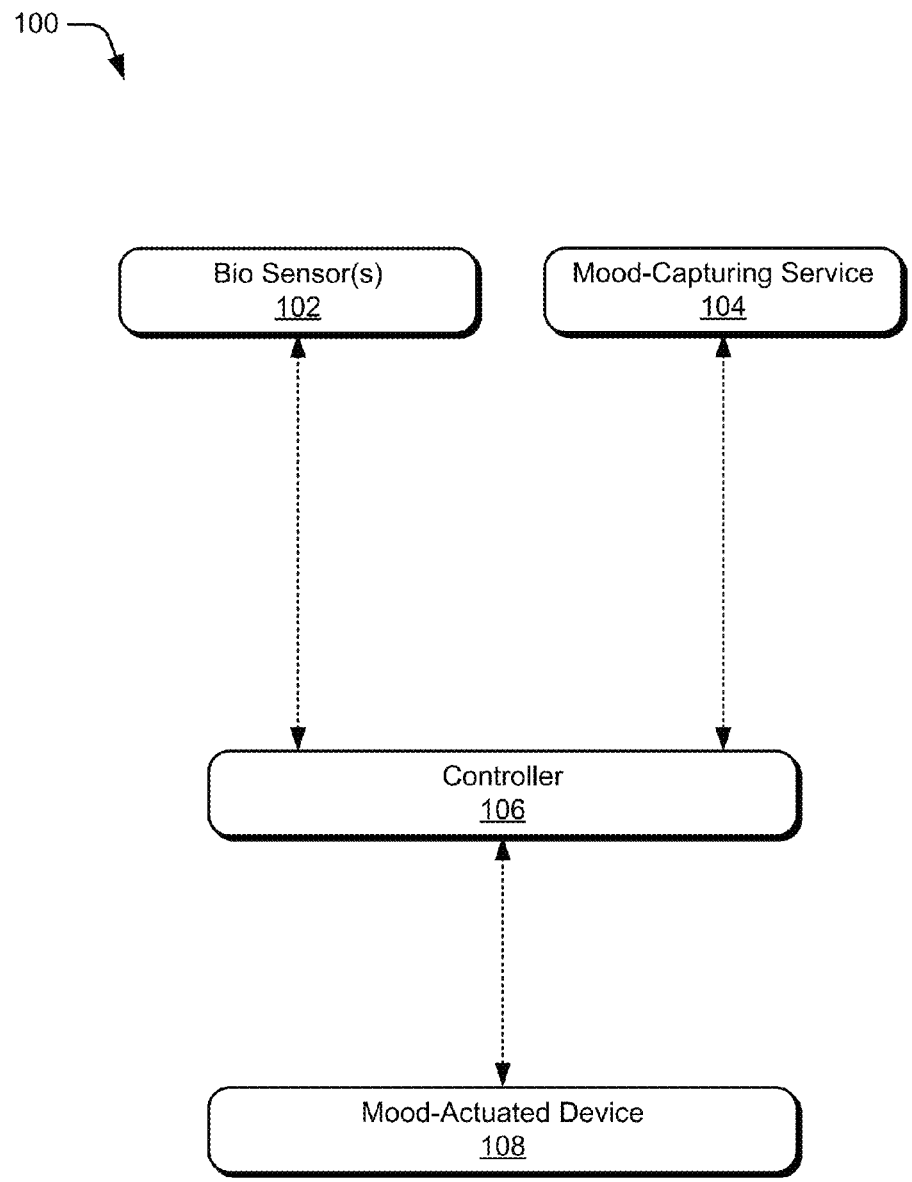
FIG. 1 illustrates an example environment in which a mood-actuated device can be implemented.

FIG. 1 is an illustration of an example environment 100 in which a mood-actuated device can be implemented. Environment 100 may include one or more bio sensors 102 and/or a mood-rating service 104. Both bio sensor 102 and mood-rating service 104 are configured to receive or sense indicators of a current mood, or emotional state, of a user, and provide mood information corresponding to the current mood or emotional state of the user to a controller 106. Environment 100 may include both bio sensor 102 and mood-rating service 104, only bio sensor 102, or only mood-rating service 104.

Bio sensor 102 can be any type of sensor configured to detect or sense indicators of a user's mood or emotional state. Bio sensor 102 can be implemented as a sensor that is configured to make physical contact with the user, such as a heart rate monitor that senses a user's heart rate, an electrocardiography monitor that senses the rate and regularity of a user's heartbeat, or a galvanic skin response monitor that senses the electrical conductance of the skin, to name just a few. Alternately, bio sensor 102 can be implemented as a sensor that does not make physical contact with the user, such as a camera or a microphone. For example, a camera sensor may be able to determine that a user is stressed based on the position of the user's eyebrows. Similarly, a microphone sensor may be able to determine that the user is stressed based on a tone of the user's voice. In some embodiments, bio sensor 102 can be configured to determine an emotional state of the user based on user interaction data received from social media, email, and/or chat applications.

After sensing the current mood of the user, bio sensor 102 provides mood information corresponding to the current mood of the user to controller 106 to enable the controller to determine an emotional state of the user. The mood information provided by bio sensor 102 may include indicators of the user's current mood or emotional state, such as changes in the user's skin temperature sensed by the galvanic skin response monitor, or changes in the user's heart rate sensed by the heart rate monitor. These indicators of the user's current mood or emotional state can then be used by controller 106 to determine the emotional state of the user. For example, an increase in the electrical conductance of a user's skin, as sensed by the galvanic skin response monitor, may be used by controller 106 to determine that the user is aroused or excited.

Mood-rating service 104 is configured to render a user interface on a display of a computing device that enables a user to rate the user's current mood or emotional state. For example, the user can rate the user's current emotional state as happy, sad, relaxed, or stressed. Mood-rating service 104 receives user-inputted data corresponding to the user's current mood via the user interface, and provides mood information corresponding to the current mood of the user to controller 106 to enable the controller to determine an emotional state of the user.

Figure 2:
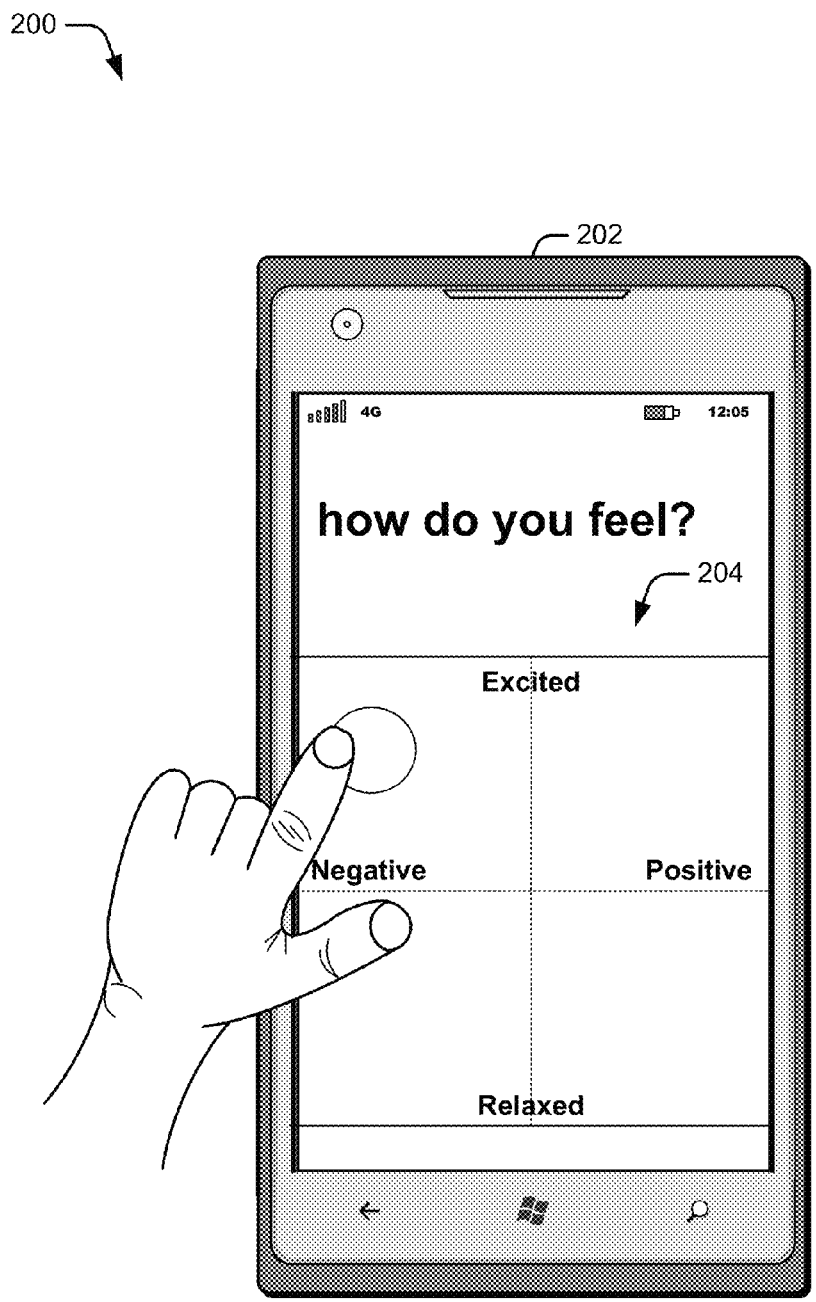
FIG. 2 illustrates a detailed example of a mood-rating service.

FIG. 2 illustrates a detailed example 200 of mood-rating service 104. In this example, mood-rating service 104 causes a computing device 202 to render a user interface 204 on a screen of the computing device. In this example, the screen is a touch-input display that is configured to receive touch-input from the user. Computing device 202 is illustrated as a mobile phone, but it is to be appreciated that computing device 202 may also be implemented as a tablet device, a communication device, an entertainment device, a gaming device, a navigation device, and/or other type of computing device. Computing device 202 can be implemented with various components, such as a processor and/or memory system to implement mood-rating service 104, as well as any number and combination of differing components as further described with reference to the example device shown in FIG. 9.

User interface 204 is configured to enable a user to rate the user's current mood. In various embodiments, the user interface includes a grid that enables the user to select between two opposite moods along a first axis, and two different opposite moods along a second axis that is perpendicular to the first axis. By way of example and not limitation, opposite moods can include happy and sad, calm and stressed, or relaxed and excited. In example 200, the user interface asks the user to respond to the question "how do you feel?" The user interface also includes a grid that enables the user to rate the user's current mood from negative valence (e.g., sad) to positive valence (e.g., happy) along a first axis (the x-axis in this example), and enables the user to rate the user's mood from excited to relaxed along a second axis (the y-axis in this example). In this example, the user has rated the user's current mood as mostly negative, and mostly excited. It is to be noted, of course, that this is just one example of a user interface that enables the user to rate the user's current mood. Mood-rating service 104 receives input indicating the current mood of the user, and provides mood information, based on the input, to controller 106 to enable the controller to determine an emotional state of the user.

Controller 106 receives mood information from bio sensor 102 and/or mood-rating service 104, and determines an emotional state of the user based at least in part on the mood information. Controller 106 can determine a variety of different emotional states of the user, such as the user being happy, sad, stressed, calm, excited, bored, or angry, to name just a few. In some embodiments, controller 106 may determine the emotional state of the user based on the received mood information and additional information, such as user history information or external information. For example, a certain heart rate value received from a heart rate monitor may indicate that a "normal" person is relaxed, but could indicate that a marathon runner, who generally has a lower resting heart rate, is stressed. Therefore, user history information corresponding to a specific user may enable controller 106 to more accurately determine the emotional state of the specific user. Additionally, external information, such as a current temperature, may be taken into account by controller 106 when determining the emotional state of the user. For example, information received from a galvanic skin response monitor indicating that the user's skin is hot may be less relevant if the temperature outside is over 90 degrees. As another example, information that the user's heart rate is high may be less relevant if external information is provided that indicates that the user is currently exercising.

After determining the emotional state of the user, controller 106 causes mood-actuated device 108 to react based on the emotional state of the user. Controller 106 can cause mood-actuated device 108 to react to correspond to a variety of different emotional states or moods of the user, including by way of example and not limitation, the user being happy, sad, stressed, calm, excited, bored, or angry. As described in more detail below, mood-actuated device 108 can be controlled to react to the emotional state of the user in a variety of different ways, such as by changing shapes, moving, making sounds, or lighting up, to name just a few.

In some embodiments, controller 106 causes mood-actuated device 108 to react to indicate the emotional state of the user. For example, if the emotional state of the user is determined to be "stressed", controller 106 causes mood-actuated device 108 to reflect that the user is stressed. In other embodiments, mood-actuated device 108 is controlled to react to help change the emotional state of the user. For example, if the emotional state of the user is determined to be "stressed", controller 106 causes mood-actuated device 108 to react in a way that may help to calm the user.

Figure 3:
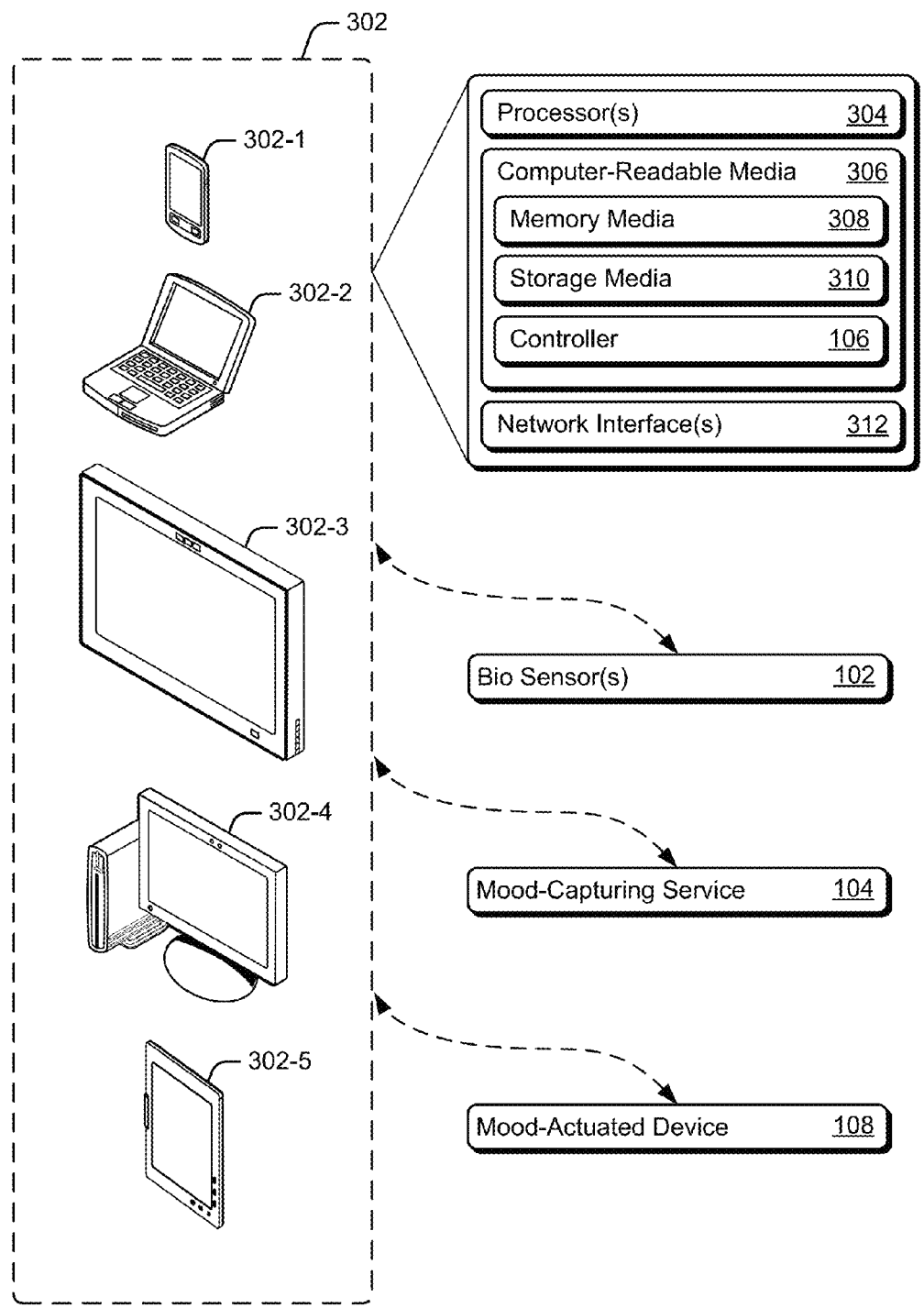
FIG. 3 illustrates a computing device in which a controller may be embodied.

FIG. 3 illustrates a device 302 in which controller 106 may be embodied. Device 302 is illustrated with various non-limiting example devices: smartphone 302-1, laptop 302-2, television 302-3, desktop 302-4, and tablet 302-5. Device 302 includes processor(s) 304 and computer-readable media 306, which includes memory media 308 and storage media 310. Applications and/or an operating system (not shown) embodied as computer-readable instructions on computer-readable media 306 can be executed by processor(s) 304 to provide some or all of the functionalities described herein. Computer-readable media 306 also includes controller 106.

Device 302 also includes, or is in communication with, one or more bio sensors 102 and/or mood-rating service 104, and mood-actuated device 108. Bio sensor 102 and mood-rating service 104 are configured to capture mood information as discussed above, and may be separate or integral with device 302. For example, in some embodiments, bio sensors 102 and/or mood-rating service 104 may be located at device 302 along with controller 106. In other embodiments, bio sensors 102 and/or mood-rating service 104 may communicate with device 302 and controller 106 over a network. Mood-actuated device 108 may also be separate or integral with device 302. For example, in some embodiments, device 302 is implemented as part of mood-actuated device 108. In other embodiments, mood-actuated device 108 may communicate with device 302 and controller 106 over a network.

Device 302 may also include network interface(s) 312 for communicating data over wired, wireless, or optical networks. Data communicated over such networks may include mood information communicated from bio sensors 102 and/or mood-rating service 104 to controller 106, as well as control signals communicated between controller 106 and mood-actuated device 108. By way of example and not limitation, network interface 312 may communicate data over a local-area-network (LAN), a wireless local-area-network (WLAN), a personal-area-network (PAN), a wide-area-network (WAN), an intranet, the Internet, a peer-to-peer network, point-to-point network, a mesh network, and the like.

Mood-Actuated Device with Flexible Material

In various embodiments, mood-actuated device 108 includes a flexible material that is controlled to react to an emotional state of a user by changing shapes or textures. The flexible material can be any type of material or fabric that can move and/or change shapes, including felt, cloth, plastic, or metal, to name just a few. In some embodiments, the flexible material is configured to hang on a wall, but it is to be appreciated that the flexible material can be designed in any size and/or shape.

Figure 4:
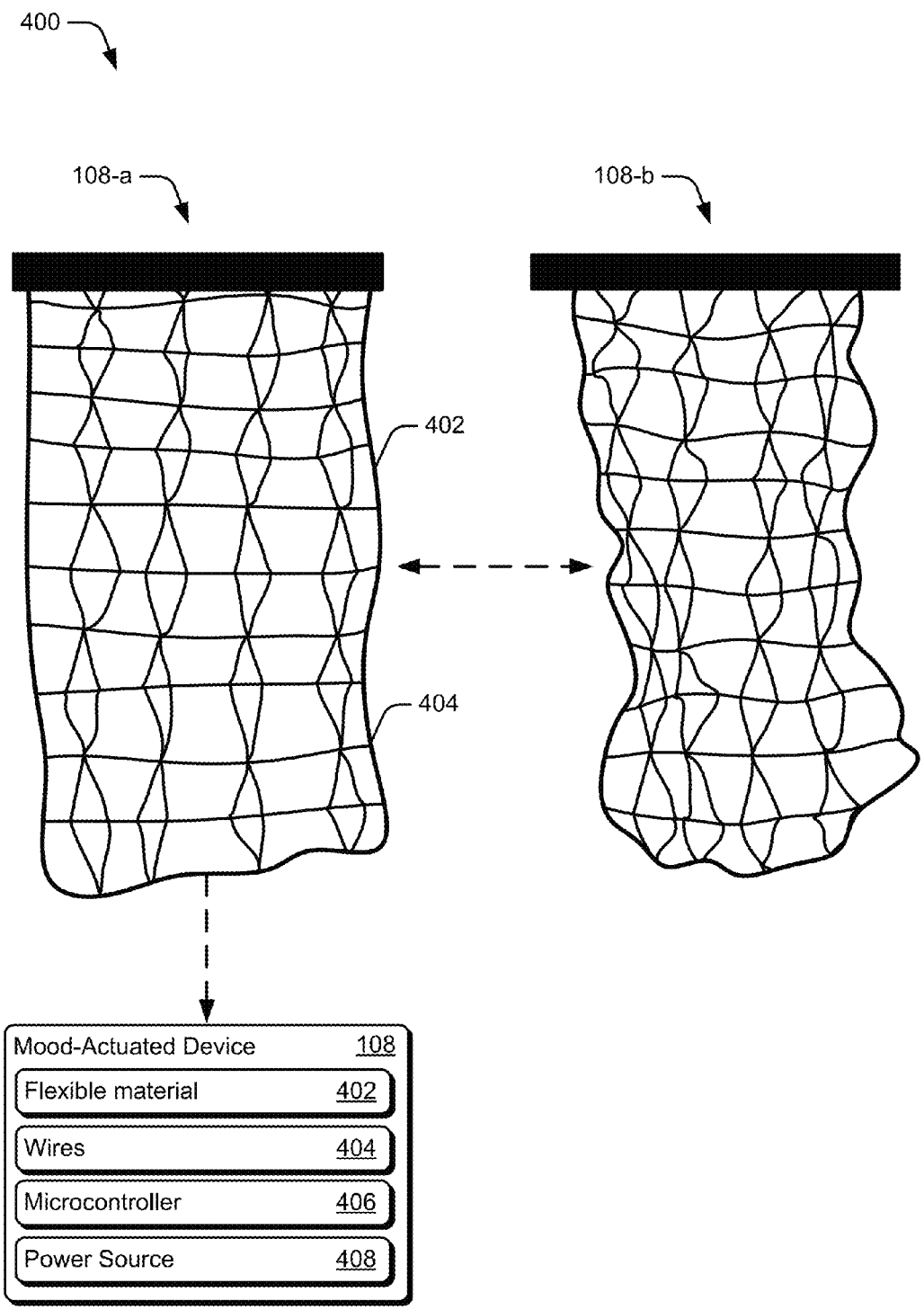
FIG. 4 illustrates a detailed example of a mood-actuated device that includes a flexible material.

FIG. 4 illustrates a detailed example 400 of mood-actuated device 108 that includes a flexible material 402. In this example, flexible material 402 of mood-actuated device 108 is controlled by controller 106 to react to a change in the emotional state of the user by changing shapes from a flat shape illustrated at 108-*a* to a crumpled or enfolded shape illustrated at 108-*b*. In some embodiments, controller 106 causes flexible material 402 of mood-actuated device 108 to react to indicate the emotional state of the user. For example, the flat shape of flexible material 402 at 108-*a* may indicate a first emotional state of the user, and the crumpled shape of flexible material 402 at 108-*b* may indicate a second emotional state of the user.

In various embodiments, flexible material 402 is controlled to indicate the emotional state of the user by changing to a shape that visually mirrors the emotional state of the user. As described herein, a shape of the flexible material visually mirrors an emotional state when characteristics of the shape represent characteristics of the emotional state. At 108-a, for example, the relaxed shape of flexible material 402 may visually mirror that the emotional state of the user is calm. In contrast, the tight winding up of flexible material 402 at 108-b may visually mirror that the user is stressed. It is to be noted, however, that mood-actuated device 108 can be configured or mapped to change to any shape responsive to any emotional state of the user. For example, flexible material 402 could be controlled to change to the crumpled shape to indicate that the user is calm, and to change to the flat shape to indicate that the user is stressed.

In an embodiment, flexible material 402 of mood-actuated device 108 is configured to react to four quadrants of high or low arousal, and negative or positive valence. For example, as described above, if the user is in a state of low arousal, or calm, flexible material 402 can be controlled to react as illustrated at 108-a, and if the user is in a state of high arousal, or stressed, the flexible material can react as illustrated at 108-b. In addition to these examples, however, flexible material 402 can be controlled to react to visually mirror happiness if the user is happy, such as by being controlled to react with rapid movements of air pockets running through the flexible material. Alternately, if the user is sad, flexible material 402 can be controlled to react to visually mirror sadness, such as by being controlled to droop. It is to be noted, however, that mood-actuated device 108 can be configured to move in any direction or change into any shape to indicate any emotional state of the user.

By changing shapes, flexible material 402 notifies the user of the user's emotional state, and enables the user to alter this state through awareness. Consider, for example, that the user is unaware of being stressed. In response to the user's stressful state, flexible material 402 is controlled to change to the crumpled shape illustrated at 108-b. This crumpled shape may cause awareness by the user that the user is stressed which enables the user to act to reduce this stress level, such as by taking a few deep breaths or going for a walk. If the user is successful in relaxing, flexible material 402 notifies the user that the user has calmed down by changing back to the flat shape. It is to be appreciated, that noticing flexible material 402 react by changing back to the flat shape at 108-a may help to reassure the user that the user's stress level has been reduced.

In some embodiments, flexible material 402 is configured to change to a shape that can help change the emotional state of the user. The shapes that can help change the emotional state of the user can be based on studies that indicate that the user's emotional state is changed by watching or interacting with the shape of the flexible material. For example, if the emotional state of the user is "stressed", controller 106 can cause flexible material 402 to react in a way that may help to calm the user such, as by causing the flexible material to slowly unfurl. Watching flexible material 402 slowly unfurl may help relax the user, thereby changing the user's emotional state from stressed to calm.

In non-limiting example 400, mood-actuated device 108 further includes wires 404, a microcontroller 406, and a power source 408. Flexible material 402 is interlaced with wires 404, which can be any type of wire that is configured to contract when heated, such as Nitinol wire. When wires 404 heat and contract, they cause flexible material 402 to react by crumpling as illustrated at 108-b. As wires 404 cool, they cause flexible material 402 to unfold and return to its original flat state as illustrated at 108-a. It is to be noted that other mechanisms may be implemented to cause the flexible material to react, such as servo motors.

Microcontroller 406 is configured to receive control signals from controller 106, and responsively cause power from power source 408 to be fed through wires 404 causing the wires to heat up and contract. For example, microcontroller 406 can turn on power source 408 for a predetermined amount of time to heat wires 404 thereby causing flexible material 402 to change to the crumpled shape at 108-b. Similarly, microcontroller 406 can turn off power source 408 to cool the wires thereby causing flexible material 402 to change back to the flat shape illustrated at 108-a. In some embodiments, mood-actuated device 108 may further include one or more hanging weights that are attached to the lower end of flexible material 402. These hanging weights help to pull flexible material 402 back to the flat shape as wires 404 cool.

Mood-Actuated Device with Mechanical Component

In various embodiments, mood-actuated device 108 includes a mechanical component that is controlled to react by moving based on the emotional state of the user. In some embodiments, the mood-actuated device is configured to be wearable by the user, and the mechanical component can notify the user, and in some cases other people, of the emotional state of the user. In these embodiments, bio sensor 102 may be implemented as part of mood-actuated device 108 to sense indicators of an emotional state of a user that is wearing the mood-actuated device. Alternately, bio sensor 102 may be implemented separate from mood-actuated device 108 and configured to communicate with mood-actuated device 108 via a wired or wireless connection.

Figure 5:
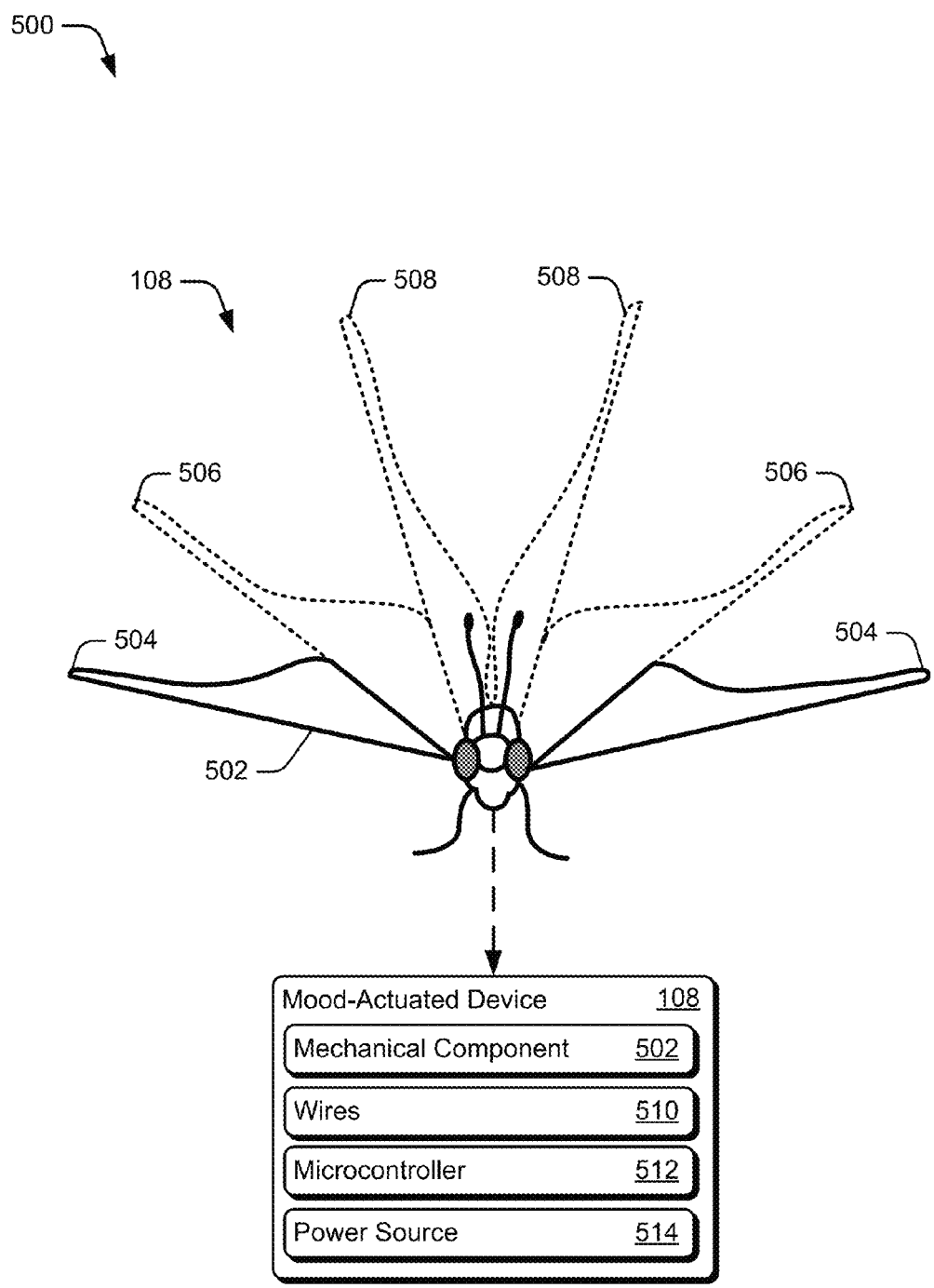
FIG. 5 illustrates a detailed example of a mood-actuated device that includes a mechanical component.

FIG. 5 illustrates a detailed example 500 of a mood-actuated device 108 that includes a mechanical component 502. In this example, mood-actuated device is implemented as a robotic butterfly, and mechanical component 502 is implemented as mechanical wings of the robotic butterfly. Mechanical component 502 of mood-actuated device 108 is controlled by controller 106 to react by moving based on the emotional state of the user.

Controller 106 can vary the speed and/or the amount of movement of mechanical component 502 to indicate the emotional state of the user. For example, at 504 controller 106 causes the wings of the robotic butterfly to move a small distance, resulting in a "gentle hover". At 506, controller 106 causes the wings of the robotic butterfly to move a greater distance than the distance moved at 504. At 508, controller 106 causes the wings of the robotic butterfly to move an even greater distance than the distance moved at 506, resulting in a "large flap" of the wings. In some embodiments, controller 106 causes mechanical component 502 of mood-actuated device 108 to react to indicate the emotional state of the user. For example, the movement of the wings of the robotic butterfly illustrated at 504 may indicate a first emotional state of the user, the movement of the wings at 506 may indicate a second emotional state of the user, and the movement of the wings at 508 may indicate a third emotional state of the user.

In various embodiments, mechanical component 502 is controlled to indicate the emotional state of the user by moving to visually mirror the emotional state of the user. As described herein, a movement of the mechanical component visually mirrors an emotional state when characteristics of the movement represent characteristics of the emotional state. For example, the gentle hover of the mechanical wings at 504 may visually mirror that the emotional state of the user is calm or relaxed. In contrast, the large flap of the wings at 508 may visually mirror that the user is stressed, excited, and/or nervous. In some cases, controller 106 can also control the speed at which mechanical component 502 moves. For example, controller 106 can control a duration of time for the full wingtip-to-wingtip contraction of the large flap at 508 to represent different emotional states of the user. To do so, controller 106 causes the wings to move slowly to increase the duration of time for the full wingtip-to-wingtip contraction, or to move quickly to decrease the duration of time for the full wingtip-to-wingtip contraction. It is to be noted that mood-actuated device 108 can be configured or mapped to any type of movement responsive to any emotional state of the user. For example, the wings could be controlled to move in the large flap of 508 to indicate that the user is calm, and to gently hover at 504 to indicate that the user is stressed.

Mechanical component 502 notifies the user of the user's emotional state through movement, and enables the user to alter this state through awareness. Consider, for example, that the user is unaware of being stressed. In response to the user's stressful state, the wings of the robotic butterfly are controlled to move in the large flap as illustrated at 508. This large flap may cause awareness by the user that the user is stressed, which enables the user to act to reduce this stress level, such as by taking a few deep breaths or going for a walk. If the user is successful in relaxing, the wings of the robotic butterfly notify the user that the user has calmed down by moving in the gentle hover as illustrated at 504. It is to be appreciated, that noticing the wings move in the gentle hover may help to reassure the user that the user's stress level has been reduced.

In some embodiments, mechanical component 502 is configured to move in a way that can help change the emotional state of the user. The movements that can help change the emotional state of the user can be based on studies that indicate that the user's emotional state is changed by watching or interacting with the movement of the mechanical component. For example, if the emotional state of the user is "stressed", controller 106 can cause mechanical component 502 to react in a way that may help to calm the user such, as by causing the wings of the robotic butterfly to move in the gentle hover. Watching the wings of the mechanical butterfly move in the gentle hover may help relax the user, thereby changing the user's emotional state from stressed to calm.

In example 500, mood-actuated device 108 further includes wires 510, a microcontroller 512, and a power source 514. In this example, the wings of the robotic butterfly are interlaced with wires 510 (not pictured), which can be any type of wire that is configured to contract when heated, such as Nitinol wire. When wires 510 are heated, they cause the wings of the robotic butterfly to close, and as wires 510 cool they cause the wings to open. Thus, microcontroller 512 causes the wings of the robotic butterfly to flap by causing power from power source 514 to be fed through wires 510 causing the wings to close, and reducing the power fed through wires 510 causing the wings to open. Microcontroller 512 can control the apex of the flap (e.g., how much the wings close) and/or the speed of the flap by modifying the voltage fed from power source 514 to wires 510. It is to be noted that other mechanisms may be implemented to cause the wings of the robotic butterfly to move, such as servo motors.

In some cases, the mechanical component can be designed so as to notify other people of the user's emotional state. For example, a mood-actuated device worn by a user could notify other people that the user is stressed by causing movement of the mechanical component. As an example, in a classroom environment, the mechanical component could notify the teacher whether or not each student is paying attention. In other embodiments, the mechanical component is configured to notify the user without notifying others of the user's emotional state. For example, the mechanical component can vibrate or move in a way that is noticeable to the user but is not noticeable by others.

Example Methods

Figure 6:
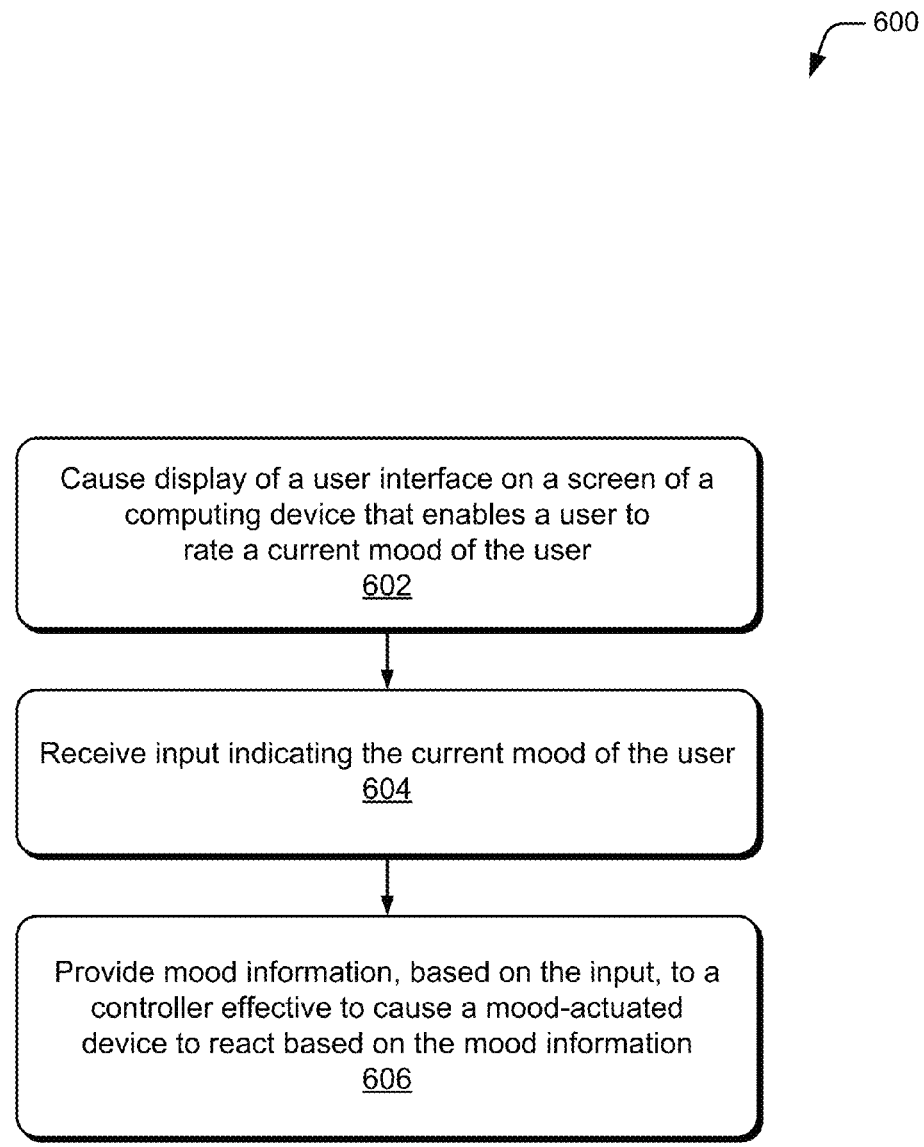
FIG. 6 illustrates an example method implemented by a mood-rating service.

FIG. 6 is a flow diagram depicting an example method 600 implemented by mood-rating service 104. Block 602 causes display of a user interface on a screen of a computing device that enables a user to rate a current mood of the user. For example, mood-rating service 104 causes a user interface 204 (FIG. 2) to be displayed on a screen of computing device 202 that enable a user to rate a current mood of the user.

Block 604 receives input indicating the current mood of the user, and block 606 provides mood information, based on the input, to a controller effective to cause a mood-actuated device to react based on the mood information. For example, mood-rating service 104 receives user input indicating the current mood of the user via user interface 204. Mood-rating service 104 then provides mood information, that includes the user input, to controller 106 effective to cause mood-actuated device 108 to react based on the mood information.

Figure 7:
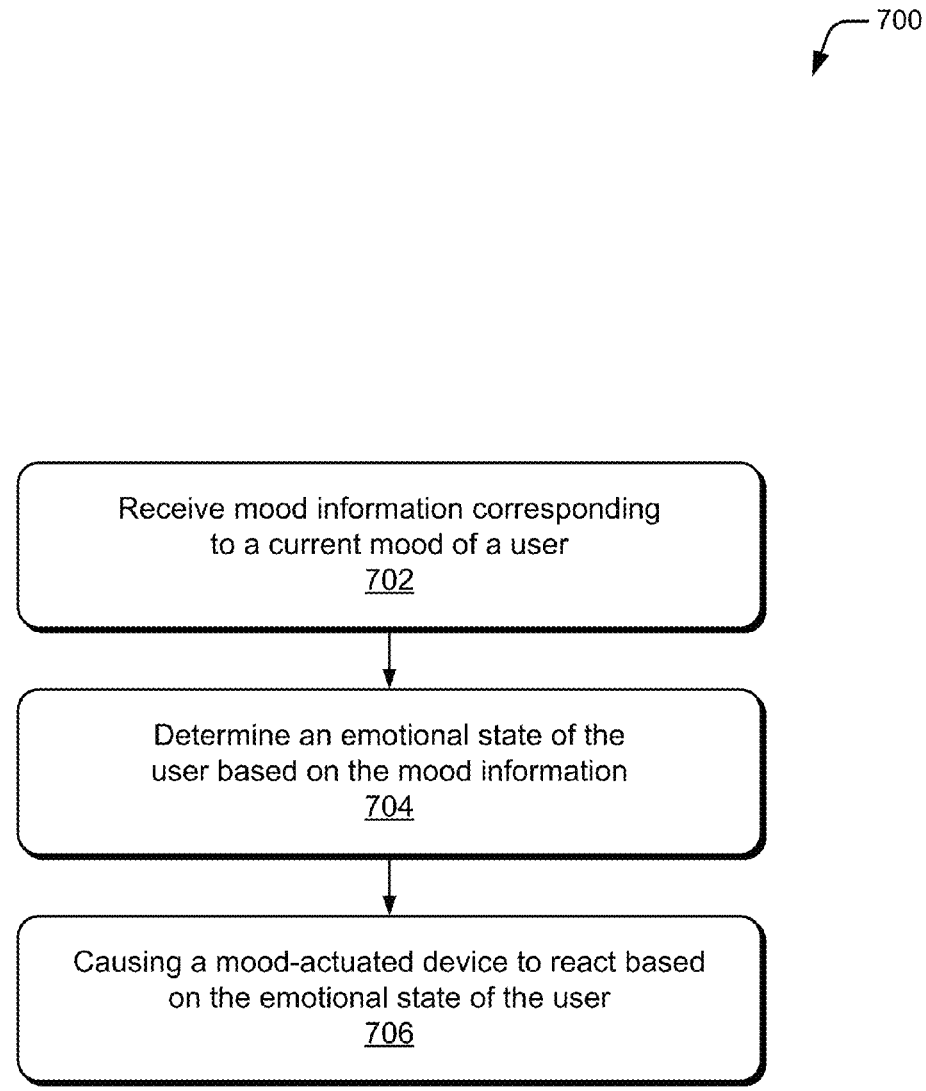
FIG. 7 illustrates an example method of controlling a mood-actuated device.

FIG. 7 is a flow diagram depicting an example method 700 of controlling mood-actuated device 108. Block 702 receives mood information corresponding to a current mood of a user. For example, controller 106 (FIG. 1) receives mood information corresponding to a current mood of the user from bio sensors 102 and/or mood-rating service 104.

Block 704 determines an emotional state of the user based on the mood information. For example, controller 106 determines an emotional state of the user based on the mood information received from bio sensors 102 and/or mood-rating service 104. Controller 106 can determine a variety of different emotional states of the user, such as the user being happy, sad, stressed, calm, excited, bored, or angry, to name just a few.

Block 706 causes a mood-actuated device to react based on the emotional state of the user. For example, controller 106 causes mood-actuated device 108 to react based on the emotional state of the user. In some cases, mood-actuated device 108 includes a flexible material 402 that is configured to react by changing to a shape that corresponds to the emotional state of the user. In other embodiments, mood-actuated device 108 includes a mechanical component 502 that is configured to react by moving based on the emotional state of the user.

Figure 8:
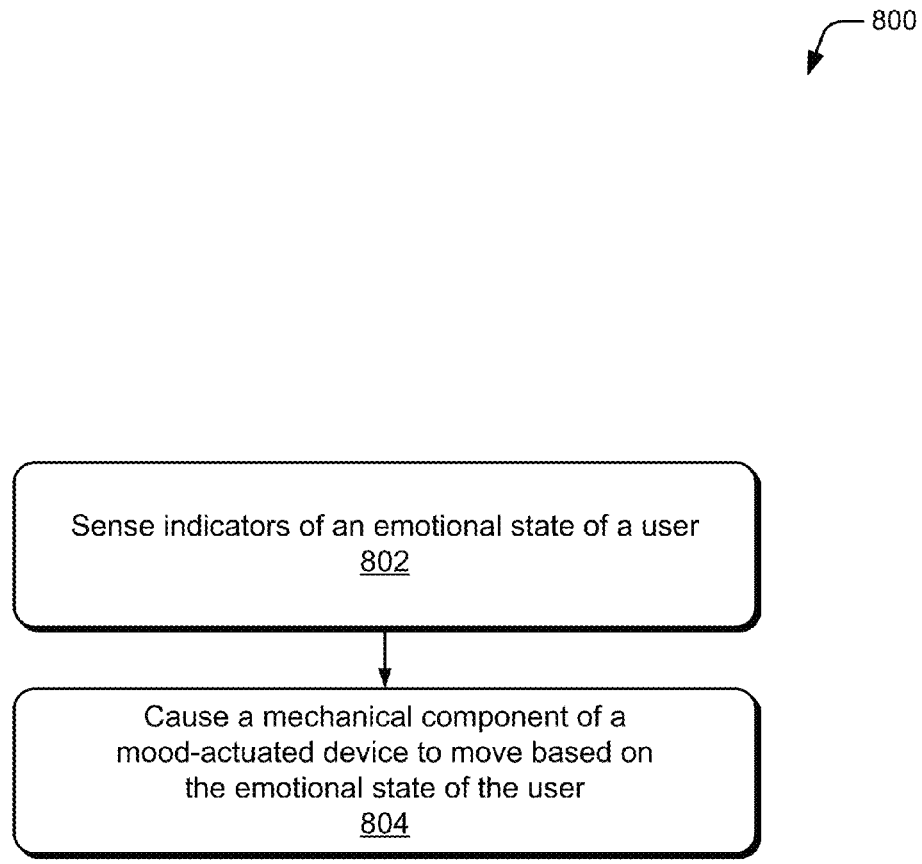
FIG. 8 illustrates an example method implemented by a mood-actuated device that includes a bio sensor.

FIG. 8 is a flow diagram depicting an example method 800 implemented by a mood-actuated device that includes a bio sensor. Block 802 senses indicators of an emotional state of a user. For example, bio sensor 102 (FIG. 1) can be implemented as part of a wearable mood-actuated device 108, such as the mechanical butterfly illustrated in FIG. 5. Bio sensor 102 can be any type of sensor configured to detect or sense indicators of a user's mood or emotional state. In this case, bio sensor 102 is implemented as a sensor that is configured to make physical contact with the user, such as a heart rate monitor, an electrocardiography monitor, or a galvanic skin response monitor.

Block 804 causes a mechanical component to move based on the emotional state of the user. For example, microcontroller 512 (FIG. 5) causes mechanical component 502 (illustrated as mechanical wings) to move based on the emotional state of the user sensed by bio sensor 102.

Example Device

Figure 9:
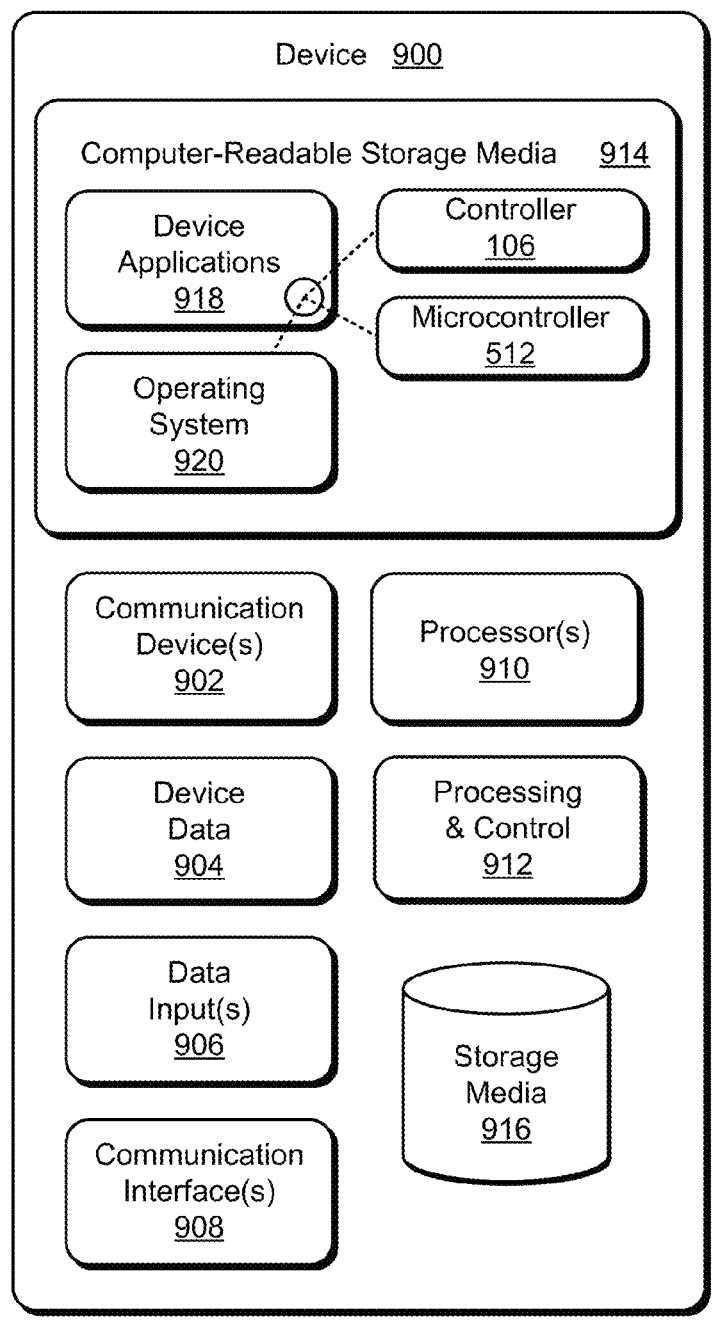
FIG. 9 illustrates an example device in which techniques for a mood-actuated device can be implemented.

FIG. 9 illustrates various components of example device 900 that can be implemented as any type of client, server, and/or display device as described with reference to the previous FIGS. 1-8 to implement techniques enabling a mood-actuated device. In embodiments, device 900 can be implemented as one or a combination of a wired and/or wireless device, as a form of flat panel display, television, television client device (e.g., television set-top box, digital video recorder (DVR), etc.), consumer device, computer device, server device, portable computer device, user device, communication device, video processing and/or rendering device, appliance device, gaming device, electronic device, and/or as another type of device. Device 900 may also be associated with a viewer (e.g., a person or user) and/or an entity that operates the device such that a device describes logical devices that include users, software, firmware, and/or a combination of devices.

Device 900 includes communication devices 902 that enable wired and/or wireless communication of device data 904 (e.g., received data, data that is being received, data scheduled for broadcast, data packets of the data, etc.). The device data 904 or other device content can include configuration settings of the device, media content stored on the device, and/or information associated with a user of the device. Media content stored on device 900 can include any type of audio, video, and/or image data. Device 900 includes one or more data inputs 906 via which any type of data, media content, and/or inputs can be received, such as user-selectable inputs, messages, music, television media content, recorded video content, and any other type of audio, video, and/or image data received from any content and/or data source.

Device 900 also includes communication interfaces 908, which can be implemented as any one or more of a serial and/or parallel interface, a wireless interface, any type of network interface, a modem, and as any other type of communication interface. The communication interfaces 908 provide a connection and/or communication links between device 900 and a communication network by which other electronic, computing, and communication devices communicate data with device 900.

Device 900 includes one or more processors 910 (e.g., any of microprocessors, controllers, and the like), which process various computer-executable instructions to control the operation of device 900 and to enable techniques for implementing a transparent display device. Alternatively or in addition, device 900 can be implemented with any one or combination of hardware, firmware, a system-on-chip (SoC), or fixed logic circuitry that is implemented in connection with processing and control circuits which are generally identified at 912. Although not shown, device 900 can include a system bus or data transfer system that couples the various components within the device. A system bus can include any one or combination of different bus structures, such as a memory bus or memory controller, a peripheral bus, a universal serial bus, and/or a processor or local bus that utilizes any of a variety of bus architectures.

Device 900 also includes computer-readable storage media 914, such as one or more memory devices that enable persistent and/or non-transitory data storage (i.e., in contrast to mere signal transmission), examples of which include random access memory (RAM), non-volatile memory (e.g., any one or more of a read-only memory (ROM), non-volatile RAM (NVRAM), flash memory, EPROM, EEPROM, etc.), and a disk storage device. A disk storage device may be implemented as any type of magnetic or optical storage device, such as a hard disk drive, a recordable and/or rewriteable compact disc (CD), any type of a digital versatile disc (DVD), and the like. Device 900 can also include a mass storage media device 916.

Computer-readable storage media 914 provides data storage mechanisms to store the device data 904, as well as various device applications 918 and any other types of information and/or data related to operational aspects of device 900. For example, an operating system 920 can be maintained as a computer application with the computer-readable storage media 914 and executed on processors 910. The device applications 918 may include a device manager, such as any form of a control application, software application, signal-processing and control module, code that is native to a particular device, a hardware abstraction layer for a particular device, and so on.

The device applications 918 also include any system components or modules to implement techniques using or enabling a mood-actuated device. In this example, the device applications 918 can include controller 106 and/or microcontroller 512 for controlling a mood-actuated device.

Conclusion

This document describes various apparatuses and techniques for implementing a mood-actuated device. Although the invention has been described in language specific to structural features and/or methodological acts, it is to be understood that the invention defined in the appended claims is not necessarily limited to the specific features or acts described. Rather, the specific features and acts are disclosed as example forms of implementing the claimed invention.

What is claimed is:

1. A robotic butterfly, comprising:
   one or more bio sensors configured to sense indicators of an emotional state of a user;
   mechanical wings configured to react based on the emotional state of the user; and
   a microcontroller configured to cause the mechanical wings to move in a first way if a first emotional state of the user is sensed by the one or more bio sensors, and to move in a second, different, way if a second emotional state of the user is sensed by the one or more bio sensors.

2. The robotic butterfly as recited in claim 1, wherein the mechanical wings are interlaced with wires that contract when heated, and wherein the microcontroller is configured to cause the mechanical wings to move by causing the wires to be heated or cooled.

3. The robotic butterfly as recited in claim 1, wherein the microcontroller is configured to cause the mechanical wings of the robotic butterfly to move in a gentle hover to indicate the first emotional state of the user, and to move in a large flap to indicate the second emotional state of the user.

4. The robotic butterfly as recited in claim 1, wherein the microcontroller is configured to cause the mechanical wings of the robotic butterfly to move at a first speed to indicate the first emotional state of the user, and to move at a second speed to indicate the second emotional state of the user.

5. A mood-actuated device, comprising:
   a bio sensor configured to sense indicators of an emotional state of a user; and
   mechanical wings configured to move based on the emotional state of the user by moving at a first speed if the bio sensor senses indicators of a first emotional state of the user and by moving at a second speed if the bio sensor senses indicators of a second emotional state of the user.

6. The mood-actuated device as recited in claim 5, wherein mood-actuated device comprises a robotic butterfly, and wherein the mechanical wings comprise wings of the robotic butterfly.

7. The mood-actuated device as recited in claim 5, wherein the mechanical wings are configured to move based on the emotional state of the user by moving in a way that is mapped to the emotional state of the user.

8. The mood-actuated device as recited in claim 5, wherein the mechanical wings are configured to move based on the emotional state of the user by moving in a way that is mapped to the emotional state of the user such that the movement visually mirrors the emotional state of the user.

9. The mood-actuated device as recited in claim 5, wherein the mechanical wings are configured to move based on the emotional state of the user by moving in a way that is designed to help change the emotional state of the user.

10. The mood-actuated device as recited in claim 5, wherein the mood-actuated device is wearable by the user.

11. The mood-actuated device as recited in claim 5, wherein the bio sensor is configured to make physical contact with the user.

12. The mood-actuated device as recited in claim 5, wherein the bio sensor comprises at least one of a heart rate monitor, an electrocardiography monitor, or a galvanic skin response monitor.

13. A method, comprising:
sensing indicators of an emotional state of a user; and
causing mechanical wings of a mood-actuated device to move based on the emotional state of the user by moving at a first speed to indicate a first emotional state of the user or by moving at a second speed to indicate a second emotional state of the user.

14. The method as recited in claim 13, wherein the mood-actuated device comprises a robotic butterfly, and wherein the mechanical wings comprises wings of the robotic butterfly.

15. The method as recited in claim 14, wherein the causing comprises causing the mechanical wings of the robotic butterfly to move at the first speed to correspond to a gentle hover to indicate the first emotional state of the user, and to move at the second speed to correspond to a large flap to indicate the second emotional state of the user.

16. The method as recited in claim 15, wherein first emotional state of the user comprises a relaxed state, and wherein the second emotional state of the user comprises a stressed state.

17. The method as recited in claim 13, wherein the mechanical wings move in a way that is designed to indicate the emotional state of the user.

18. The method as recited in claim 13, wherein the mechanical wings move in a way that is designed to visually mirror the emotional state of the user.

19. The method as recited in claim 13, wherein the mechanical wings move in a way that is designed to help change the emotional state of the user.

* * * * *